United States Patent [19]

Boiarski et al.

[11] Patent Number: 5,191,206
[45] Date of Patent: Mar. 2, 1993

[54] DISTRIBUTED FIBER OPTIC SENSOR USING CLAD MATERIAL LIGHT BACKSCATTERING

[75] Inventors: Anthony A. Boiarski, Columbus; Vincent D. McGinniss, Sunbury, both of Ohio

[73] Assignee: Electric Power Research Institute, Inc., Palo Alto, Calif.

[21] Appl. No.: 685,858

[22] Filed: Apr. 16, 1991

[51] Int. Cl.⁵ .................. H01J 5/16; G01K 11/00; G02B 6/00
[52] U.S. Cl. .......................... 250/227.14; 374/161; 385/12
[58] Field of Search ........... 250/227.14, 231.1, 227.16; 374/161, 131; 385/12, 13; 356/44

[56] References Cited

U.S. PATENT DOCUMENTS

| | | | |
|---|---|---|---|
| 4,151,747 | 5/1979 | Gottlieb et al. | 356/44 |
| 4,201,446 | 5/1980 | Geddes et al. | 350/96.29 |
| 4,316,388 | 2/1982 | Miller et al. | 374/161 |
| 4,505,542 | 3/1985 | Clarke | 356/44 |
| 4,714,829 | 12/1987 | Hartog et al. | 374/161 |
| 4,729,627 | 3/1988 | Saito et al. | 374/161 |
| 4,830,513 | 5/1989 | Grego | 374/131 |
| 5,052,820 | 10/1991 | McGinnis et al. | 374/161 |

FOREIGN PATENT DOCUMENTS

| | | | |
|---|---|---|---|
| 0069131 | 3/1987 | Japan | 374/161 |
| 2140554 | 11/1984 | United Kingdom | 374/131 |

OTHER PUBLICATIONS

Hartog et al., "A Fiber-optic Temperature Distribution Sensor", Colloquium on Optical Fiber Sensors, London, England, May 1982.
A. H. Hartog, J. of Lightwave Tech. LT-1, 498-509 (1983) "A Distributed Temperature Sensor Based on Liquid-Core Optical Fibers".
J. P. Dakin, et al., Elect. Lett., 21 (13), 569-570 (1985) "Distributed Optical Fiber Raman Temperature Sensor Using a Semiconductor Light Source and Detectors".
A. H. Hartog, et al., Elec. Lett., 21 (32), 1061-1062 (1985) "Distributed Temperature Sensing in Solid Core Fibers".
K. Ogawa, et al., Springer Proceedings in Physia, vol. 44, "Optical Fiber Sensors", Springer-Verlag Berlin (1989) A Fiber-Optic Distributed Temperature Sensor with High-Distance Resolution.
M. Gottlieb and G. B. Brandt, Appl. Opt. 20, 3867-73 (1981) "Temperature Sensing in Optical Fibers Using Cladding and Jacket Loss Effects".
A. J. Rogers, "Distributed Optical-Fibre Sensors", J. Phys. D: Appl. Phys. 19, 2237-55 (1986).

Primary Examiner—David C. Nelms
Assistant Examiner—Michael Messinger
Attorney, Agent, or Firm—Watkins, Dunbar & Pollick

[57] ABSTRACT

A distributed fiber-optic sensor is obtained by using cladding that produces a change in the intensity of scattered light in the cladding of an optical fiber in response to a change in the environment of the cladding. The change in clad scattered light is coupled into the core causing a change in the intensity of backscattered light in the core. A sensing means such as an optical time domain refractometer is used to determine the change in intensity of the core backscattered light at a specific location along the fiber. The change in intensity of the scattered light in the clad is caused by overall changes in the amount of light in the cladding and changes in the number, size or both of the refractive index inhomogeneities in the cladding. These inhomogeneities can be, but are not limited to, composition variations, density variations of the same composition, phase separations, voids, or particulate inclusions.

32 Claims, 6 Drawing Sheets

DISTRIBUTED FIBER OPTIC SENSOR USING CLAD MATERIAL LIGHT BACKSCATTERING

FIELD OF THE INVENTION

The present invention relates to distributed fiber optic sensing devices that are capable of detecting environmental changes along the entire length of the optical fiber. More particularly, this invention relates to a method of sensing environmental changes along the length of the optical fiber by taking advantage of scattering in the clad material. This scattered light is coupled back into the core and contributes to the overall backscattered light intensity resulting in improved backscattering signal measurements.

BACKGROUND OF THE INVENTION

A wide variety of sensors, including temperature sensors, have been developed using fiber optics. In a great many of these sensors, the length of the optical fiber serves only as a transmission means and not as the sensor itself, the sensor typically being separate from the optical fiber or located only at the tip of the fiber. Such sensors are referred to here as point sensors. The sensor may or may not involve light phenomena. For example, U.S. Pat. No. 4,848,923 (Jul. 18, 1989) to Ziegler et al. uses a fiber/optic to transmit light pulses that are obtained by converting electrical pulses from a pulse generator wherein the pulse gaps change in relation to an environmental change such as temperature. Here the sensor involves electrical pulses not light phenomena.

In some instances, the point sensor is not a temperature sensor; rather compensation must be made for temperature changes that may cause erroneous readings. For example, U.S. Pat. No. 4,487,206 (Dec. 11, 1984) to Aagard is a point optical pressure sensor that uses fiber optics to carry transmitted light to the end of the fiber and two optical fibers to return reflected light to a detector, one fiber to return light from a reflecting pressure sensitive lens-diaphragm-mirror combination and the second fiber to return reflected reference light. Such an arrangement compensates for temperature and fiber bending changes. U.S. Pat. No. 4,613,811 (Sep. 23, 1986) to Vaerewyck et al. discloses a point magneto-optical current sensor that uses a fiber optic to transmit and receive a light signal that is compensated for temperature, loop degradation, and linearity in a Faraday current sensor. U.S. Pat. No. 4,724,316 (Feb. 9, 1988) to Morton discloses a point fiber optic sensor that depends on changes in the curvature of a fiber optic wave guide caused by a mechanical force, e.g. a cam, to produce variations in light intensity in the fiber optic. Coating materials and support members are provided so as to minimize thermal stress. U.S. Pat. No. 4,639,138 (Jan. 27, 1987) to Martin et al. is a fiber-optic, rotation-rate, point sensor that uses two optic fiber loops to eliminate temperature-dependent index of refraction and fiber length sensitivity.

There are many point sensors for the detection of temperature. The optical fibers involved (other than at the tip or end of the fiber) serve only to conduct light signals and are not a part of the sensor. For example, U.S. Pat. No. 4,574,172 (Mar. 4, 1986) to Burack et al. uses an optical cable as a radiation input source for a two color pyrometer that is used to determine and control brazing temperature. U.S. Pat. No. 4,672,199 (Jun. 9, 1987) and 4,758,087 (Oct. 27, 1987) to Anderson et al. uses an optical fiber to conduct light to a sensor with a reflective surface responsive to temperature or pressure changes. Bimetallic strips are used for temperature sensing.

U.S. Pat. No. 4,758,087 (Jul. 19, 1988) to Hicks, Jr. uses a resonant cavity formed from an optical fiber segment and coupled to an input and output fiber to measure external conditions such as temperature and pressure. U.S. Pat. No. 4,749,254 (Jun. 7, 1988) to Seaver discloses an optical point sensor that relies on an optical filter to detect the wavelength shift of the band edges of various optical and infrared filters with changes in temperature, pressure and index of refraction of the environment. The sensor uses an optical fiber transmission link. U.S. Pat. No. 4,883,062 (Nov. 28, 1989) to Nicholson shows a point detector consisting of an interference edge filter mounted on the end of an optical fiber. The transition slope of the edge filter curves shifts depending on changes in the parameter measured. Reflected light from the edge filter is passed through an interference bandpass filter that has an edge slope intersecting the slope of the edge filter. Shifts in the slope of the edge filter, due to measured parameter variation, result in a change in the intensity of light passing to a detector. U.S. Pat. No. 4,703,175 (Oct. 27, 1987) to Salour et al. discloses a point fiber optic sensor in which light is transmitted through semiconductor material that absorbs a portion of the light as a function of temperature. U.S. Pat. No. 4,790,669 (Dec. 13, 1988) to Christensen also uses a semiconductor material at the end of an optical fiber to determine changes in reflected light caused by temperature changes in the semiconductor material.

U.S. Pat. No. 4,714,342 (Dec. 22, 1987) to Jackson et al. is a temperature point detector that measures the interference pattern of reflected signal and reference beams. Thermal expansion of the sensor fiber produces a dimensional change in the fiber giving rise to a phase shift between the reference and signal beams. U.S. Pat. No. 4,708,494 (Nov. 24, 1987) to Kleinerman uses a point detector with a luminescent material that has a temperature-dependent absorption coefficient. Excitation light is directed to the sensor through an optical fiber. The resulting luminescence light intensity is a function of temperature.

U.S. Pat. No. 4,750,139 (Jun. 7, 1989) to Dils discloses a temperature sensor that uses a black body emitter to emit light with a flux density proportional to temperature. The light is transmitted through optical fibers to a detection system. An optical light pipe or a pyrometer may also be used as the input for the system. U.S. Pat. No. 4,794,619 to Tregay discloses an optical temperature probe that uses the thermal emission from a recess in the tip of an optical temperature detection device. U.S. Pat. No. 4,859,079 (Aug. 22, 1989) to Wickersheim et al. uses a blackbody sensor to direct radiation to an infrared sensor that is in communication with an optical sensor that uses a luminescent material. Light is directed to the luminescent material from a detector and the temperature modified light is than returned to the detector using an optical fiber. U.S. Pat. No. 4,752,141 (Jun. 21, 1988) to Sun et al. also uses a sensor having luminescent material that is excited by light carried along an optical fiber with the resultant luminescent radiation being returned to a detector along the optical fiber. U.S. Pat. No. 4,459,044 (Jul. 10, 1984) to Alves uses a temperature sensitive phosphor material at the end of an optical fiber to detect temperature changes by passing ultraviolet radiation from a source through the optical fiber to the phosphor and then detecting the visible radiation returned from the phosphor through the optical fiber. U.S. Pat. No. 4,789,992 (Dec. 6, 1988) to Wickersheim et al. uses a luminescent material placed on the surface of an object whose temperature is to be measured. The luminescent material is excited by light from an optical fiber and the resultant luminescent radiation is returned to a detector through the optical fiber. U.S. Pat. No. 4,223,226 (Sep. 16, 1980) to Quick et al. uses a phosphor material at the end of an optical fiber to detect temperature change. The phosphor receives incident light stimulation from an optical fiber and the emitted phosphorescent radiation, of which the amplitude decay rate and wavelength are functions of temperature, is transmitted to a detector through the input fiber or a separate optical fiber. U.S. Pat. No. 4,749,856 (Jun. 7, 1988) to Walker et al. is a point sensor that relies on the changes in optical transmission properties of polymeric materials in response to changes in temperature, humidity, pressure, sound, etc.

By inserting one or more point sensors along the optical fiber it is possible to obtain measurement of the physical property at the point of location of the sensor along the optical fiber. Such intermittent sensors are termed "quasi-distributed" sensors. For example, U.S. Pat. No. 4,201,446 (May 6, 1980) to Geddes et al. uses a short section of a temperature-sensitive liquid core or liquid cladding optical fiber inserted in series with a conventional optical fiber to determine temperature based on a reduction in the intensity or numerical aperture after the light passes through the temperature-sensitive liquid region. U.S. Pat. No. 4,861,979 (Aug. 29, 1989) to Tardy et al. is a quasi-distributed sensor in which a gap is introduced at successive points along the length of the fiber, i.e., the fiber becomes a series of discrete segments with a gap between each segment. The gap is filed with a medium that is sensitive to the physical parameter being measured, e.g., temperature, such that the coefficient of reflection from the end (optical surface) of each segment and the intensity of a returned light pulse depend on changes in the gap medium. An appropriate reception circuit allows measurement of the physical parameter at each gap along the fiber.

Another methodology for measuring temperature is what is termed "distributed" fiber sensing in which the parameter to be measured can be determined along the entire length of the fiber. In one form of distributed fiber sensing, termed intrinsic fiber sensing, properties of the fiber itself are used to detect various physical parameters including temperature as they effect a portion or all of a fiber along its length. For example, U.S. Pat. No. 4,362,057 (Dec. 7, 1982) to Gottlieb et al. takes advantage of the fact that when a fiber is heated, the thermal radiation emitted will depend on the temperature, emissivity of the fiber material, and the spectral range of the wavelength being observed. Both the temperature and position of the hot spot along the fiber can be determined. U.S. Pat. No. 4,295,739 (Oct. 20, 1981) to Meltz et al. uses a multicore optical fiber to determine temperature or strain changes along the length of the fiber as a result of cross-talk between adjacent cores in the fiber. U.S. Pat. No. 4,647,203 (Mar. 3, 1987) to Jones et al. uses an optical fiber Fabrey-Perot interferometer that is sensitive to any parameter that influences the optical fiber's length, e.g., temperature, magneto-strictive effects, etc. U.S. Pat. No. 4,659,923 (Apr. 21, 1987) to Hicks, Jr. uses a dual path optical fiber to sense a relative change in the propagation constant as a result of an applied force that produces an interference variation. The applied force can be a change in temperature or pressure. U.S. Pat. No. 4,830,513 (May 16, 1989) to Grego uses the backscattered radiation from the fiber core itself to measure temperature variations along the fiber. The use of an optical time domain reflectometer allows the temperature information to be associated with the backscattering point along the fiber. The methodology is based on frequency spectrum variations in the backscattered radiation from the fiber core with respect to incident radiation.

The concept of distributed fiber sensing has also been discussed in the non-patent literature. The most active area of distributed fiber optic sensing has been temperature measurement with at least one review article having appeared on the topic. A. J. Rogers, "Distributed Optical-Fibre Sensors", J. Phys. D: Appl. Phys. 19, 2237-55 (1986). The most practical of the distributed sensor concepts use Optical Time Domain Reflectometry (OTDR) to monitor backscattered light from segments of the fiber along its entire length.

For the OTDR approach, the distance of any particular change in the backscattered light can be calculated by measuring the elapsed time of the returned pulse. If the time required to propagate back and forth is $\tau$, then the location, L, of the change is given by $$L = \frac{c\tau}{2n} \tag{1}$$

where
c = velocity of light in vacuum ($3 \times 10^8$ m/s), and
n = refractive index of the fiber.

To use the OTDR approach as the basis for a distributed fiber optic sensor, the key is to modify an ordinary optical fiber along its entire length so that the modification results in a fiber where the local loss or backscattering characteristics or both are changed by changes in a particular parameter, e.g., temperature. By monitoring the amount of change in the local backscattered light characteristics using the OTDR methodology, environmental changes can be measured along the entire fiber length. Furthermore, the point (in time) of the maximum or minimum OTDR signal change can be used to identify the location (in space) of the maximum or minimum parameter value.

The OTDR signal consists of light backscattered during the progress of a pulse traveling down the fiber sensor. The amount of backscattered light, $P_{bs}(l)$, from a given location l along the fiber, within the scattering element dx, can be written as $$P_{bs}(l) = 1/2 P_o \Delta t v_g C_s NA^2 \exp\left(\int_o^l -2\alpha dx\right) \tag{2}$$

where $P_o$ is the power launched into the fiber, $\Delta t$ the source pulse width, and $v_g$ the pulse group velocity. The term NA in Equation (2) is the fiber's local numerical aperture (i.e., light capturing efficiency), which is dependent on the index of refraction of the core and clad materials. In Equation (2), $C_s$ and $\alpha$ are the scattering constant and the total loss coefficient, respectively.

In order to use the backscattered light pulse intensity in a distributed temperature sensor, it is clear from Equation (2) that $\alpha$, $C_s$ or NA must be dominant functions of temperature.

Based on the theory of D. Gloge, "Weakly Guiding Fibers", Applied Optics, 10 (10), 2252-58 (1971), $C_s$ and $\alpha$ can be written as follows:

$$C_s = (\alpha_R)_{co} + (\alpha_s)_{co} + P_{cl}/P_T(\alpha_s)_{cl} \quad (3)$$

$$\alpha \approx \alpha_{co} + P_{cl}/P_T(\alpha_{cl}). \quad (4)$$

In Equation (3) and (4), $\alpha_R$ is the Raman scattering coefficient and $\alpha_s$ is the Rayleigh scattering coefficient. Subscripts co and cl are associated with the core and cladding, respectively. The factor $P_{cl}/P_T$ is the fraction of propagating power that exists in the cladding due to evanescent wave effects.

Researchers at Southampton University, M. C. Farriers and M. E. Fermann, "Temperature Sensing by Thermally Induced Absorption in a Neodymium Doped Optical Fibre", Proceedings of SPIE, Fiber Optic Sensors, The Hague, Netherlands, Vol. 798, 115-117 (1987), produced a distributed temperature sensor based on temperature attenuation of the core glass, i.e., $(\alpha_s)_{co}$ in Eq. (3). The fiber core was doped with neodymium and a 904 nm pulsed laser source was used to obtain distributed temperature sensor data. At this wavelength, the temperature dependent core absorption $\alpha_{co}(T)$ was found to be linear over a 50° C. increment. Although the doped-fiber concept appears feasible, doping non-uniformity problems and the need to produce special fiber preforms prior to sensor fabrication appear to have dampened interest in this methodology.

The first demonstration of a distributed fiber optic sensor used a special fiber having a liquid core, A. H. Hartog, "A distributed Temperature Sensor Based on Liquid-Core Optical Fibers", J. of Lightwave Tech. LT-1, 498-509 (1983). In this case, increasing the fiber temperature causes an increase in the scattering coefficient of the liquid core, $(\alpha_s)_{co}$, by 0.02 dB/° C. for the length of fiber tested. Although workable, the liquid core fibers have not been accepted since producing the sensor requires a large deviation from standard fiber manufacturing technology.

Scattering in optical fibers is caused principally by the Rayleigh effect which results from inhomogeneities in the core glass that are formed in the production process. This type of scattering is at the same wavelength (elastic) as the incident light and core scattering is largely independent of temperature changes (except for liquid core fibers described). However and as noted above, Grego (U.S. Pat. No. 4,830,513) has taken advantage of this intrinsic property by comparing frequency spectrum variations between backscattered and incident radiation due to temperature variation.

There is a small (100-1000 times less) contribution to the scattered power from the Raman effect, $\alpha_R$ in Equation (3), which originates from molecular and crystalline effects within the core glass. A key attribute of the Raman effect is that it results in temperature-dependent scattering at a different wavelength than the incident light, i.e., inelastic. Raman scattering has received the most attention as a method of providing a distributed fiber optic temperature sensing (DFOTS) system. Commercial devices are being supplied by several companies.

Initial Raman work was carried out in Great Britain which led to a practical device incorporating solid state components, J. P. Dakin, et al., "Distributed Optical Fiber Raman Temperature Sensor Using a Semiconductor Light Source and Detector", Elect. Lett., 21 (13), 569-570 (1985). In this case, the ratio of Raman Stokes to anti-Stokes scattering intensity was used to determine temperature along the sensor length independent of attenuation losses. York Technology, A. H. Hartog, et al., "Distributed Temperature Sensing in Solid Core Fibers", Elec. Lett, 21 (32), 1061-1062 (1985), measured the anti-Stokes backscattered light from the fiber and used a different referencing scheme to cancel attenuation effects.

Efforts have recently been made to reduce the spatial resolution to about 1 meter using narrow pulsed laser sources. K. Ogawa, et al., "A Fiber-Optic Distributed Temperature Sensor With High-Distance Resolution", Springer Proceedings in Physia, Vol 44, Optical Fiber Sensors, Springer-Verlag Berlin (1989). However, the fact that Raman scattering produces such a weak signal limits resolution capability.

Equations (2) through (4) indicate that for negligible cladding attenuation or scattering effects, and constant core scattering and attenuation properties, the change in NA with temperature can be used to form a DFOTS system. In this case, Equation (2) becomes $$P_{bs}(l) \approx NA(T) \exp(-2\alpha l) \quad (5)$$

where $$NA \approx \sqrt{2n_{co}\Delta n} \quad (6)$$

and $$\Delta n = n_{co} - n_{cl}. \quad (7)$$

From Equation (6) and (7), it can be seen that the proper choice of core and cladding materials, such that $\Delta n$ decreases with increasing temperature, will result in a decreasing NA(T) and $P_{bs}(l)$. This is accomplished by noting the index change with temperature, $dn/dT$, of various materials and using these special materials (glasses or polymers) to provide the temperature sensor.

A changing NA approach has been suggested for providing a DFOTS Systems. However, the technique does not appear to be practical since only special material selections will provide the proper combination of refractive index changes. Such special material selections can introduce other problems such as fiber pulling irregularities. Sensor cost can be high if nonstandard glasses are used.

Since there is evanescent wave penetration of guided light into the cladding, low-loss clad material is normally chosen to keep the overall fiber loss coefficient ($\alpha$) as small as possible. The clad contribution to overall loss is shown in Equation (4) as $P_{cl}/P_T(\alpha_{cl})$ where $\alpha_{cl}$ is the clad loss coefficient and $P_{cl}/P_T$ is the fraction of power traveling in the clad material. D. Gloge, "Weakly Guiding Fibers", Applied Optics, 10 (10), 2252-58 (1971), has shown that $P_{cl}/P_T$ term can be written as:

$$P_{cl}/P_T = 2\lambda/[3\pi a(2n_{co}\Delta n(T))^{\frac{1}{2}}] \quad (8)$$

where

λ = wavelength of incident light source and
a = radius of fiber core.

As the core or clad index changes with temperature, such that $\Delta n(T)$ changes, more or less power is present in the cladding. Therefore, more or less fiber transmission loss will occur according to Equation (4).

The clad attenuation DFOTS technique was described theoretically by M. Gottlieb and G. B. Brandt, "Temperature Sensing in Optical Fibers Using Cladding and Jacket Loss Effects", Appl. Opt. 20, 3867–73 (1981), and is the subject of U.S. application 059,545 assigned to the same assignee as the present invention, and which is herein incorporated by reference.

SUMMARY

The present invention solves many of the prior art problems involved with distributed fiber optic sensors by taking advantage of the contribution to backscattered light that is caused by scattering in the clad material. A portion of the clad material light scattering is coupled back into the core and contributes to the overall backscattered light intensity. The present invention is based on changes in the backscattered light arising mainly from Rayleigh scattering changes in the fiber cladding material. The amount of change is proportional to the environmental parameter to be measured so that a distributed sensor is formed. A key advantage is that Rayleigh scattering is 100 to 1000 times more intense than the Raman scattering intensity from a typical fiber. This increased intensity provides for improved spatial resolution in backscattering signal measurements.

In its basic form, the present invention is a distributed fiber-optic sensor that consists of an optical fiber core with a cladding that produces a non-attenuated change in the intensity of backscattered light in the optical fiber core in response to a change in the environment of the cladding. By a non-attenuated change in intensity is meant a change that is not due to an abnormal or irreversible loss of light from the core/cladding system such as takes place when the transmitted light is irreversibly absorbed into the cladding due to an environmental change. A sensing means is used in conjunction with the distributed fiber-optic sensor to determine the change in the intensity of the backscattered light.

The non-attenuated, cladding-produced change in intensity of backscattered light (in response to a change in the environment of the cladding) appears to be caused by two design features: The first feature consists of refractive index inhomogeneities in the cladding. These inhomogeneities can be, but are not limited to, composition variations, density variations of the same composition, phase separations, voids, or particulate inclusions. The refractive index inhomogeneities are responsive to environmental changes and, as a result, produce a change in the intensity of the backscattered light in the optical fiber core. The refractive index inhomogeneities may change in number or in size or both in response to an environmental change. The second feature is the overall amount of light traveling in the cladding. This is determined by the refractive index of the cladding. By selecting an appropriate cladding material with a bulk refractive index that is sensitive to environmental change, a change in the intensity of the backscattered light from the cladding is produced when the refractive index of the cladding changes in response to an environmental parameter.

The change in intensity of the backscattered light in the core is thought to be due primarily to changes in Rayleigh scattering in the cladding brought about, as noted above, by 1) refractive index inhomogeneities, 2) the amount of light traveling in the cladding, or 3) both of these features. However, it is possible that other types of clad scattering such as Mie scattering could also influence the intensity of the backscattered light in the optical fiber core.

As noted, changes in the backscattered light in the core are dominated and controlled by changes in the amount of scattering from the cladding. However, these scattering changes in the cladding do not cause significant transmission losses in the core. Transmission loss due to the cladding is essentially negligible. Transmission losses occurring in the core/cladding system are essentially due to and dominated by losses occurring in the fiber core.

The present invention is distinguished from point sensors where the optical fiber serves only as a transmission means with the sensor being separate from or located only at the tip of the optical fiber. The present invention is also distinguished from quasi-distributed fibers where one or more point sensors are intermittently located along the length of the optical fiber. In the present invention, the parameter to be sensed can be detected along the entire length of the fiber and thus the present invention is characterized as a distributed fiber-optic sensor.

Preferably the sensing means for determining the change in intensity of the backscattered light is also capable of determining the position along the length of the optical fiber where the change in intensity of the backscattered light due to a change in the environment of the cladding occurs. One sensing means capable of determining both the positions of a scattering change and the intensity of the change is an optical time domain reflectometer based on standard optical time domain reflectometry (OTDR) technology.

As is typical of optical fibers, the refractive index of the cladding material must be lower than the refractive index of the core. Under initial environmental conditions, the difference in refractive index of the cladding and the core can be in a range of about 0.005 to 0.05. As the difference becomes less than 0.005, the fiber becomes weakly guiding and losses can occur with increasing distortions due to, for example, bending and flexing of the fiber.

For a cladding whose refractive index decreases with increasing values of the environmental parameter, it is desirable to have the refractive indexes of the cladding and core material as close to one another as possible at the initial or normal operating environment of fiber. Thus, at initial conditions with a cladding whose refractive index decreases with an increase of the environmental parameter, such as temperature, the difference between the refractive index of the core and the cladding should be in the range of about 0.005 to about 0.05 with a range of about 0.01 to about 0.03 being preferred.

It is possible to have a cladding material whose refractive index increases with increasing environmental parameter in which case it is desirable to have the difference between the refractive indexes of the core and cladding as great as possible under initial or normal operating conditions. In such a case, the core and cladding refractive indexes must approach each other as the environmental parameter increases.

If the refractive index of the cladding is sufficiently different from the core throughout the entire range of environmental parameter change, the amount of evanescent light entering the cladding is relatively constant and the intensity of the backscattered light is nearly unchanged. Thus the refractive index of the cladding must be close to the refractive index of the core at some point over the range of the environmental parameter to be measured.

It is desirable that the refractive index of the core material remain essentially constant, that is, the core material should typically change by less than about $2 \times 10^{-4}$ over the range of the changing environmental parameter. The core refractive index change may be either an increase or a decrease in refractive index over the range of change in the environmental parameter.

For relatively good measurement response, the refractive index of the cladding should undergo a change of refractive index of about 0.01 in response to a predetermined range of environmental change. Thus, if the environmental variable is temperature and the range of temperature change is 150° C., then the refractive index of the cladding should change by 0.01 over the 150 degree temperature range.

A cladding refractive index change of 0.02 in response to the predetermined environmental variable range is preferred while a cladding refractive index change of more than 0.07 over the range of environmental parameter is more preferred.

Viewed from a slightly different perspective, the refractive index of the cladding should be changing at a rate that is at least 100 times as fast as the rate of change of the refractive index of the core. A cladding refractive index rate of change that is 200 times the rate of change of the core refractive index is preferred while a refractive index rate of change of 700 times the rate of the core refractive index change is more preferred. As has been noted, these rates of change must be set with some value, typically an initial or final value, of the refractive index of the cladding less than but close to the value of the refractive index of the core and changing from that value at a rate sufficient to give measurable results.

To give a more specific example, temperature has been chosen as the environmental variable. Thus in response to a temperature change, the core refractive index should be chosen so as to be confined to a rate of change of $1 \times 10^{-6}/°$ C. This change may be an increase or a decrease of the refractive index. Given such a change in the core, the refractive index of the cladding should change by more than about $1 \times 10^{-4}/°$ C. A change of more than $3 \times 10^{-4}/°$ C. is preferred and a change of more than $7 \times 10^{-4}/°$ C. is more preferred.

The cladding material appears to give the best results when it is less than about $5.0 \times 10^{-3}$ inches thick. A thickness in the range from about $1.5 \times 10^{-3}$ to about $3.0 \times 10^{-3}$ inches thick is preferred. Generally the cladding must be thick enough to prevent power loss yet not so thick as to cause second order effects.

Typically the coating (cladding) is applied as a liquid and then polymerized using ultraviolet light or heat. As noted previously, the cladding must have a refractive index that is less than the refractive index of the core material and must produce a change in the backscattered light in the optical fiber that is responsive to a change in an environmental parameter. A typical cladding formulation is composed of a polymer, a crosslinker, and a photoinitiator. A filler composed of small particles can be added to the composition so as to provide the necessary refractive index inhomogeneities in the cladding. Such particles are of a size to provide effective Rayleigh scattering, typically less than about one-tenth to ten times the wavelength of the light being scattered. Preferably the filler should have a refractive index that is less than the cladding formulation over the range of cladding refractive index change. Typical fillers include teflon or quartz particles with a size of less than about 5 microns.

For the largest scattering effect, the refractive index of the filler must be lower than the effective refractive index of the other components of the cladding formulations where it is to be understood that the various components of the formulations combine to give a cladding with a single refractive index, i.e., an effective refractive index. Moreover, it appears that for the best scattering effect, it is the cladding formulation that undergoes a refractive index change in response to an environmental change rather than the filler.

Although the use of a light scattering filler is preferred, it is possible to achieve backscattering sensitive to an environmental parameter without the use of a light scattering filler. When a filler is not used, the scattering can be due to composition or density variations in the formulation. For example, the use of 1,6 hexanediol diacrylate (HDDA) in the formulation gives rise to backscattering, the intensity of which is responsive to an environmental parameter such as temperature. It is felt that the HDDA may retain its initial refractive index and not combine with the other components to give an overall effective refractive index. As such, the HDDA retains a local refractive index that is imbedded in the matrix formulation of the cladding. This local refractive index center, along with a matrix formulation of the cladding that is responsive to the environmental parameter, gives rise to a backscattering component in the core that is responsive to an environmental change of the cladding.

A suitable cladding formulation contains a urethane acrylic polymer, a diacrylate monomer, a triacrylate monomer and a UV curing agent. The actual coating compositions can be varied between about 5 to about 88 percent by weight for the polymer, diacrylate and triacrylate components. All cladding compositions contain about 2 percent by weight of a photoinitiator. The foregoing and other advantages of the invention will become apparent from the following disclosure in which one or more preferred embodiments of the invention are described in detail and illustrated in th accompanying drawings. It is contemplated that variations in procedures, structural features and arrangement of parts may appear to a person skilled in the art without departing from the scope of or sacrificing any of the advantages of the invention.

BRIEF DESCRIPTION OF THE DRAWINGS

FIG. 4A is representative of a core/cladding material exposed to an environmental factor under normal conditions, e.g., room temperature where $P_{cl}/P_T$ is about 1.0%. FIG. 4B is representative of a core/cladding material in an elevated environmental condition, e.g., a temperature of about 100° C. where $P_{cl}/P_T$ is about 0.65%. FIG. 4C is representative of a core/cladding material in a lowered environmental condition, e.g., a temperature of about 0° C. where $P_{cl}/P_T$ is about 1.2%.

In describing the preferred embodiment of the invention which is illustrated in the figures, specific terminology is resorted to for the sake of clarity. However, it is not intended that the invention be limited to the specific terms so selected and it is to be understood that each specific term includes all technical equivalents that operate in a similar manner to accomplish a similar purpose.

Although a preferred embodiment of the invention has been herein described, it is understood that various changes and modifications in the illustrated and described structure can be affected without departure from the basic principles that underlie the invention. Changes and modifications of this type are therefore deemed to be circumscribed by the spirit and scope of the invention, except as the same may be necessarily modified by the appended claims or reasonable equivalents thereof.

DETAILED DESCRIPTION OF THE INVENTION AND BEST MODE FOR CARRYING OUT THE PREFERRED EMBODIMENT

In patent application 07/393,977, assigned to the assignee of this application, and which is herein incorporated by reference, a distributed fiber optic sensor was described that was based on a transmission loss mechanism. The fiber was coated with a cladding material that underwent a change in its index of refraction with a change in environmental parameter such as temperature. Specifically the index of refraction of the cladding material changed so as to become greater than the index of refraction of the core material. As a result of this change in refractive index, some of the transmitted light in the core was permanently lost into the cladding material.

Figure 1A:
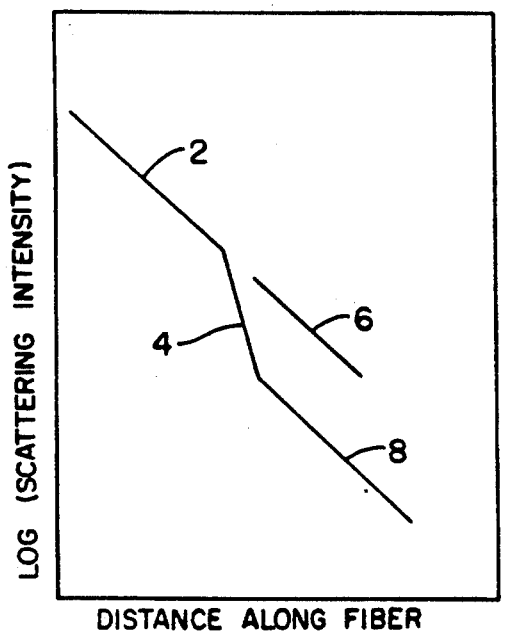
FIG. 1A is an optical time domain reflectometry (OTDR) response for a fiber optic sensor where a transmission loss mechanism is operative. The log of the backscattering intensity in dB is plotted on the vertical axis against the distance along the fiber on the horizontal axis.

The transmission loss mechanism is more fully illustrated in FIG. 1A which graphs the log of the intensity of backscattered light from the cladding with respect to the distance along the fiber. The physical embodiment from which the graph of FIG. 1A is derived is shown in FIG. 2. As seen in FIG. 2, input light 16 enters the fiber core 10 and for the most part is reflected from the cladding 14 and continues through the fiber as transmitted light 18. A small amount of the input light 16 is scattered by scattering centers in the core 10 and is returned as backscattered light 26. It is the log of the intensity of this core backscattered light that is being plotted on the vertical axis of FIG. 1.

For that segment of the plot denoted as 2 in FIG. 1A, the environmental parameter (e.g., temperature) is held constant. The negative slope of the curve at 2 indicates a decrease in the intensity of the backscattered light 26 with fiber length. This decrease is reflective of the fact that light scattering losses occur in the core which reduces the amount of transmitted light. The amount of backscattered light 26 is proportional to the intensity of the propagating light 18 in the core 10. In view of the light scattering losses in the core, the intensity of the backscattered light 26 decreases with fiber length. Thus, for the approach described in patent application 07/393,977, the dominant backscattered light source was due to scattering in the fiber core (26) and the dominant attenuation was due to clad attenuation.

Segment 4 of the plot in FIG. 1A corresponds to a hot spot in the fiber, i.e., a heated segment of the fiber. As a result of this heating (or other environmental change), the cladding described in the above referenced previous application becomes nearly opaque. Rather than being nearly totally reflected from the cladding 14 as happened in the first segment 2 of the plot, the light is absorbed into the cladding 14 and is lost from the system. This loss may be quantified as the difference between the extension 6 of the initial line segment 2 and line 8 which represents the backscattering intensity loss after the fiber is returned to its initial temperature. It is noted that the slopes of segments 2 and 8 are identical since they represent sections of the fiber that are at the same temperature but that the two segments 2 and 8 are offset by the loss of intensity of the propagating beam 16 resulting from the absorption of light into the opaque cladding 14 brought about by the temperature change.

In effect, at the first temperature (segment 2), the refractive index of the cladding 14 was less than the core material 10 and most of the transmitted light 16 was reflected from the core/cladding interface 22 and retained within the core fiber 10. As the temperature of the cladding 14 increased, the refractive index of some of the phases of the cladding 14 increased beyond the refractive index of the core allowing the transmitted light 16 in the core fiber 10 to pass into the cladding 14 rather than being reflected back into the core 10. The transmitted light 16 passing into the cladding material 14 was lost from the system and was no longer available for propagation in the core and resultant core backscattering. Thus, a temperature increase produced a loss in the intensity of the backscattered light as shown in FIG. 1A by the difference between segments 6 and 8. Because of the decrease in the amount of light in the fiber core 10 due to the losses resulting from a change in the refractive index of the cladding 14, the total amount of power (light intensity) in the core was substantially less and, as a result, less propagating light was available to be scattered from the scattering centers in the core material 10 so the core backscattering 26 decreases. Thus, for the approached described in patent application 07/393,977, the dominant backscattered light source was due to scattering in the fiber core (26) and the dominant attenuation was due to clad attenuation.

To achieve the transmission loss in the previous invention, the cladding was composed of discrete phases of organic polymers and inorganic additives that were essentially transparent to light at a first temperature but nearly opaque to light when heated to a second temperature. As a result, large amounts of light were lost from the system when a segment of the cladding was heated so as to turn the cladding into an opaque transmission light absorber.

In the present invention, the backscattered light is dominated by scattering in the cladding and transmission loss is dominated by the fiber core. Thus the present invention does not operate by a transmission loss mechanism but rather by a much different mechanism. As shown in FIG. 2, the present invention is based on the backward scattering of light by the cladding material 14 which changes in response to a change in the environmental parameter of the cladding 14. This backward scattering phenomenon does not attenuate (change the transmission of) the forward propagating beam so the small component of backscattering from the core (26) is constant. The change in clad scattering is accomplished in two ways: (1) by changing the refractive index of the cladding which changes the amount of light traveling in the cladding, specifically noting that the refractive index of the cladding 14 is always less than the refractive index of the core material 10, and (2) by varying the scattering centers in the cladding material 14, e.g. number, size or both. Thus by changing the refractive index of the cladding or the number of scattering centers in the cladding or both, it is possible to obtain a change in the amount of backscattering occurring at a particular point along the optical fiber due to a change in an environmental parameter. The amount of light in the core fiber 10 is practically unchanged in the region of the environmental change in the cladding 14. When the cladding material returns to its former environmental surrounding, the intensity of backscattering from the cladding 14 returns to its former level.

Figure 1B:
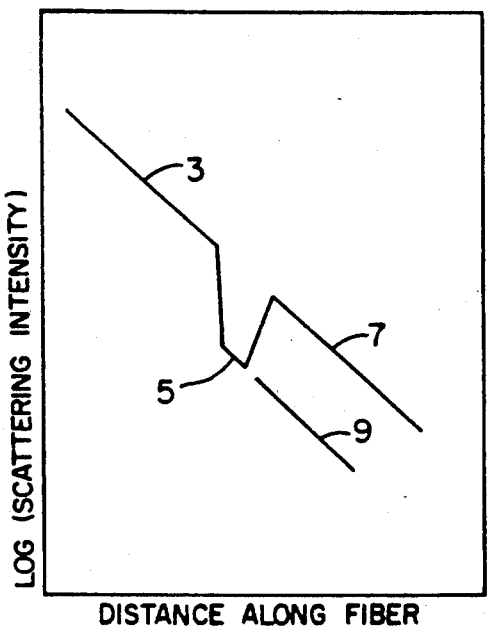
FIG. 1B is an OTDR response for a fiber optic sensor of this invention where a transmission loss mechanism is not operative, but a scattering change mechanism is operative. The log of the backscattering intensity in dB is plotted on the vertical axis against the distance along the fiber on the horizontal axis.
Figure 2:
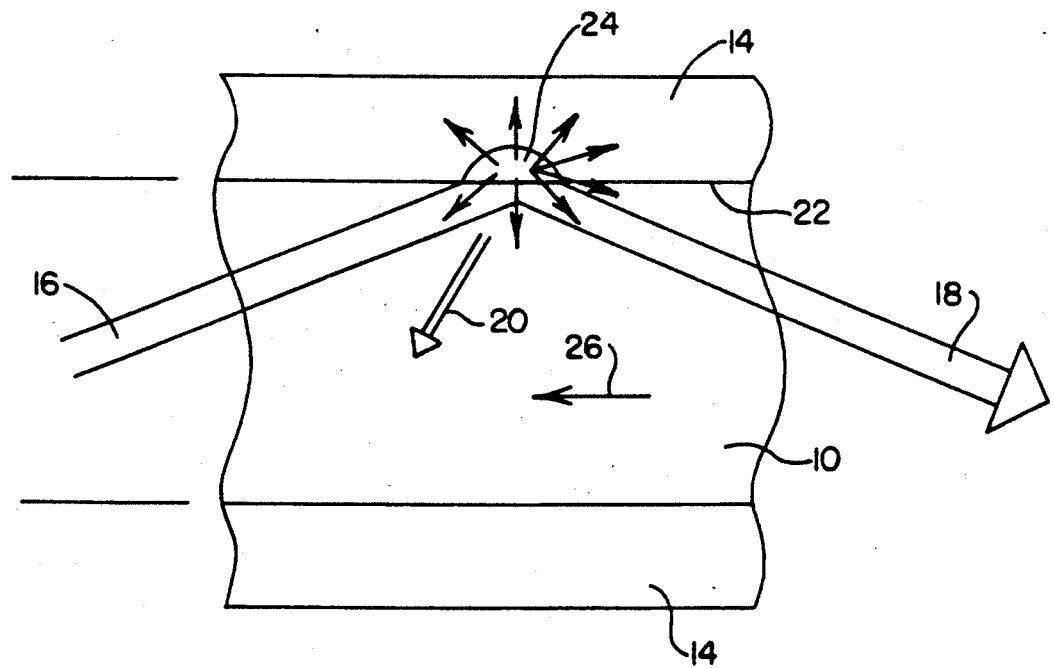
FIG. 2 is a pictorial representation showing the light interaction at the core/clad interface.

This is more fully illustrated in FIG. 1B, where the intensity of the backscattered light is seen to decrease along the distance of the fiber as shown by the decreasing slope of segment 3. This is due to the normal losses that occur along any fiber due to absorption and scattering effects that occur mainly in the fiber core.

The backscattered light change in a hot spot region is not due to scattering in the core glass 10 since core scattering changes only minimally with an environmental change such as a change in temperature. Rather, the backscattered light change in the hot spot region comes mainly from the cladding 14 and is coupled back into the core 10. This is clearly shown in FIG. 1B where an applied hot spot causes a decrease in the intensity of the backscattering as shown at segment 5. However, rather than continuing at the reduced intensity level slope denoted by segment 9 when the fiber is returned to normal or room temperature, the intensity level slope returns to its former level as shown by segment 7. Thus the hot spot intensity loss 5 is due to a change in the fraction of light being backscattered into the core rather than a loss of light from the core as was the case with the transmission loss system of FIG. 1A.

This is exemplified more fully in FIG. 2, where it is seen that a small fraction 24, $P_{cl}/P_T$, of the total light power, $P_T$, exists in the cladding. This small fraction of light 24 in the cladding 14, the so called evanescent light, usually is less than 1% of the total transmitted light intensity. However, the small amount of light that exists in the cladding 14 can be scattered by refractive index inhomogeneities such as small particles, phase irregularities and density inhomogeneities in the cladding material. The amount of backscattered light $I_{bs}$, 20, is given by the following equation:

$$I_{bs} \alpha \frac{P_{clad}}{P_{Total}} \alpha \frac{P_{cl}}{P_T} \qquad (1)$$

As a result, the more light that is present in the cladding 14, the more scattering 20 that will occur. Hence, the more light that will be coupled back into the fiber 10 which produces more backscattered light in the fiber core. Note that the clad scattered light (20 in FIG. 2) dominates the core scattered light 26.

According to the theory of Gloge (D. Gloge, "Weakly Guiding Fibers", Appl. Optics, 10, No. 10, pp. 2252-2258 (1971)), the term $P_{cl}/P_T$ in equation (1) is a function of the following parameters:

$$P_{cl}/P_T = (\lambda/a)(1/NA) \qquad (2)$$

where
a = radius of the fiber core
λ = wavelength of input light and
NA = local numerical aperture of the fiber.

Although the following set of equations are illustrated for an environmental parameter of temperature, it is to be understood that other environmental parameters could be substituted for the temperature component. Thus the term NA in equation (2) can be written:

$$NA(T) = \sqrt{n_1^2 - n_2^2(T)} \approx \sqrt{2n_1 \Delta n(T)} \qquad (3)$$

where $$\Delta n = \Delta n_o - \frac{dn_2}{dT}(T - T_o). \qquad (4)$$

In Equations (3) and (4)
T = local fiber temperature,
$T_o$ = a reference temperature, e.g., 25° C.,
$n_1$ = core refractive index (essentially constant),
$n_2$ = clad refractive index (varies with temperature),
$\Delta n_o = (n_1 - n_2)_o$ where $n_{10}$ and $n_{20}$ are the core and clad refractive indices at the reference temperature, $T_o$, e.g., 25° C. and
$dn_2/dT$ = rate of change in the clad index with temperature.
Combining the above equations, gives:

$$I_{bs} \alpha \frac{\lambda}{a} \frac{1}{\sqrt{2n_1 \Delta n(T)}} \quad (5)$$

$$\Delta n(T) = \Delta n_o - dn_2/dT(T - T_o). \quad (6)$$

Figure 3:
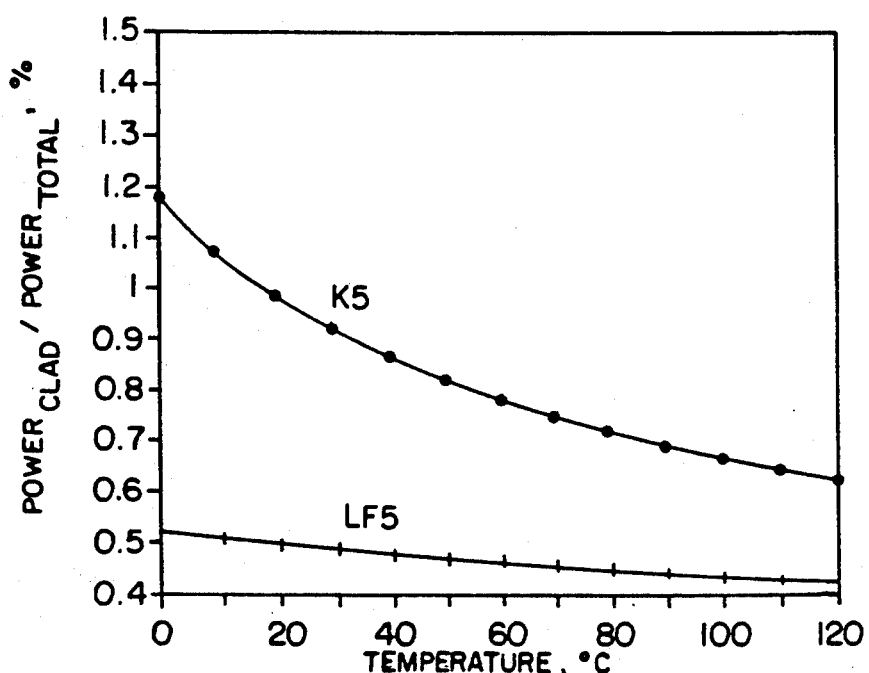
FIG. 3 illustrates the importance of material property choices. The fraction of the amount of power in the cladding to the total power ($P_{clad}/P_{Total}$) in percent is plotted on the vertical axis versus the temperature in °C. along the horizontal axis of a K5 and a LF5 core and a cladding from a typical formulation of this invention.

Equations (5) and (6) indicate that the most important parameters which govern the environmental parameter (temperature) sensitivity of the present concept are $\Delta n_o$ and $dn_2/dT$. That is, $\Delta n_o$, the difference in the core and clad refractive index at a reference temperature and $dn_2/dT$, the rate of change of the clad index with temperature govern the utility of the present invention. The importance of a relatively small difference of refractive indexes of the core and cladding materials, that is, the importance of the $\Delta n_o$ term in equation (6) is illustrated in FIG. 3. FIG. 3 shows two different core materials, K5 and LF5 with the same representative cladding material of this invention. For the K5 core, $\Delta n_o$ is 0.022 and, as seen in FIG. 3, the percentage of the light in the cladding with respect to the total power varies considerably over the temperature range from 0° to 120° C. However, when the differences between the refractive indexes of the core and cladding are much higher, as for example, with a LF5 core and the same representative cladding ($\Delta n_o = 0.082$), the change in power in the cladding with respect to the total power is much less over a segment of an environmental parameter such as temperature. Thus to provide a sensor that is responsive to environmental changes, it is essential that the core refractive index must be close to the cladding refractive index at some point of the range of the environmental parameter to be measured. The properties of the materials used in FIG. 3 are further detailed in Table 1.

TABLE 1

| \multicolumn{4}{c}{PROPERTIES OF REPRESENTATIVE CORE AND CLAD MATERIALS} |
| Materials | Function | 20° C. Refractive Index | dn/dT |
|---|---|---|---|
| TF[1] | clad | 1.498 | $-3.4 \times 10^{-4}$ |
| K5 | core | 1.520 | ~0 |
| LF5 | core | 1.580 | ~0 |

[1]Typical formulation of this invention

It is noted that for a specific clad material (fixed $dn_2/dT$), the choice of core glass material is very important to provide a sensor that will be responsive to temperature changes. FIG. 3 shows that $\Delta n_o$ must be small. In other words, the core glass refractive index, at an initial environmental parameter, must be close to the cladding refractive index. It is obvious from Equation (6) that a large value of $dn_2/dT$ would also be required to provide a sensitive temperature response. Finally, FIG. 3 shows that since the power in the cladding decreases with increasing temperature then the backscattering intensity also decreases with increasing temperature.

Figure 4A:
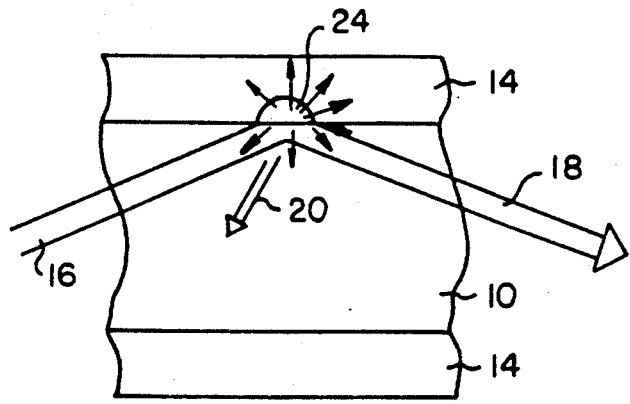
FIGS. 4A, 4B, and 4C are schematic drawings showing the clad scattering mechanism for producing a fiber optic temperature sensor.
Figure 4B:
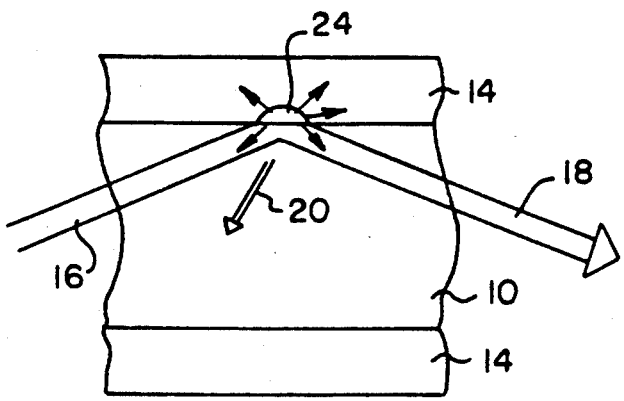
Figure 4C:
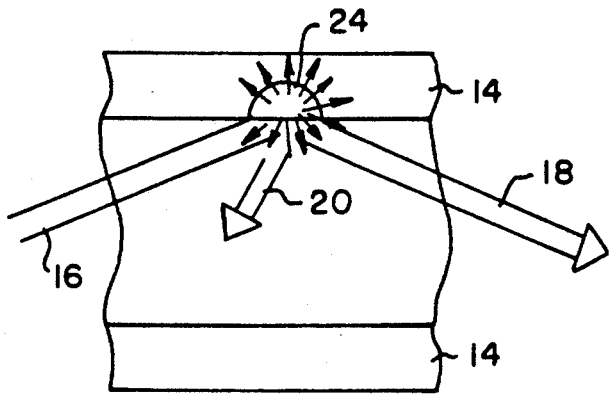

The temperature dependent scattering effect of Equations (5) and (6) is illustrated in FIGS. 4A-4C. FIG. 4A illustrates the amount of backscattering at a normal or representative environmental parameter, e.g., a room temperature of 20° C. In this instance, a moderate percentage of light 24 exists in the cladding 14 so that a moderate amount of backscattered light 20 results. As the fiber and clad material are heated, the index difference $\Delta n(T)$ increases because $dn/dT<0$, so $P_{cl}/P_T$ decreases as shown in FIG. 4B. In this instance, less light 24 exists in the clad 14 so that less scattering results and the backscattered light intensity 20 diminishes.

If the fiber clad material is cooled below the reference temperature, $\Delta n(T)$ decreases and $P_{cl}/P_T$ increases. As shown in FIG. 4C, this increased light intensity 24 in the clad 14, results in increased clad scattering and, hence the backscattered light intensity 20 is increased over that found under the reference parameter conditions (FIG. 4A).

Figure 5:
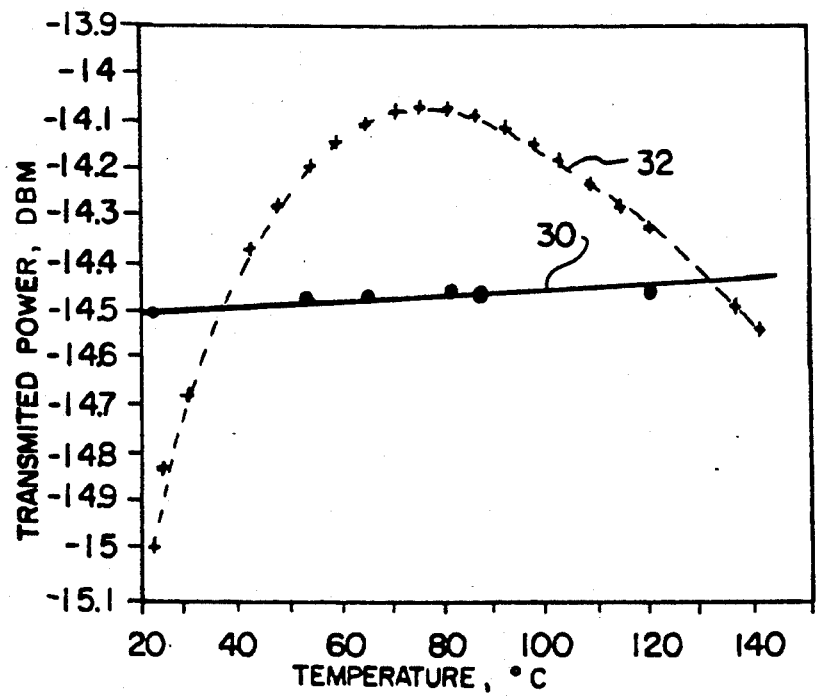
FIG. 5 gives transmission data for thick and thin clad fiber sensors. Transmission power in dBm is given on the vertical axis with temperature in °C. given on the horizontal axis.

FIG. 5 illustrates fiber transmission properties with respect to an environmental parameter such as temperature. Specifically a K5 glass fiber core was coated with a polymeric material to form a prototype fiber optic temperature sensor. An 820 nm light source was used to determine the transmission and backscattering properties of a one meter length fiber. Two types of cladding material were examined, a thin cladding (15-30 microns thick) 30 and a thick clad fiber (0.5 mm thick) 32. The thick clad fiber 32 was formed by coating additional cladding material over the thin clad fiber using a potting procedure. The thin clad fiber 30 shows no loss characteristics with temperature. In fact, there is a slight increase in transmission with increasing temperature. This increase is due to an increase in the numerical aperture (NA) of the fiber. FIG. 5 clearly shows that the thin clad fiber does not operate by a loss mechanism.

On the other hand, the thick clad fiber 32 shown in FIG. 5 indicates unusual behavior with temperature. At first, the transmission increases approximately one dB for the one meter of heated fiber length. At approximately 80° C., the transmission begins to fall, i.e., losses occur, and the loss continues to increase (transmission decreases) from 80° to 150° C. However, the loss never exceeds the value at 20° C. This unusual behavior of the thick clad fiber 32 is probably due to bending losses induced by thermal stress in the fiber. Thus it appears to be important to keep the fiber cladding thin so as to avoid this problem.

Figure 6:
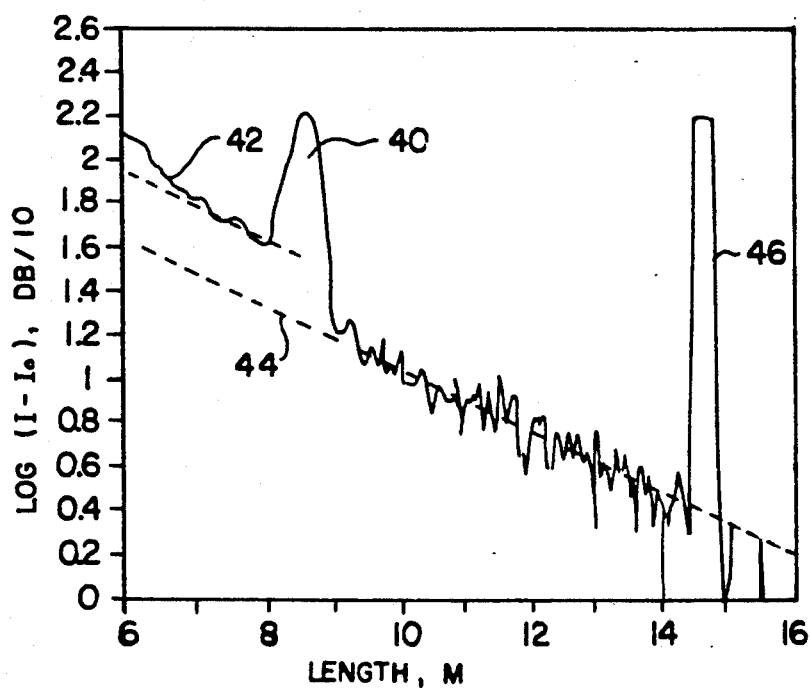
FIG. 6 shows OTDR data for a cooled fiber sensor (50 cm of fiber cooled to 0° C.) with the log $(I-I_o)$, dB/10 plotted against length, in meters.

A K5 core glass fiber with a thin cladding formulation was further examined using an optical time domain refractometer (OTDR) to measure the backscattered light intensity from a 14.5 m long fiber. First a 50 cm portion of the fiber 40 was cooled to 0° C. (ice bath). The resulting OTDR measurement is shown in FIG. 6. In this instance, there is a large (7.0 dB) increase in scattered light intensity from the cooled portion of the fiber (9 m from fiber input). The increase in local backscattered intensity was much more dramatic than expected. Following the increase in backscattered light, there was a return to the normal fiber loss slope 44 but a fixed loss of 2.5 dB was produced (difference between lines 42 and 44). This fixed loss is caused by the fact that the numerical aperture (NA) of the fiber is reduced in the cold spot region. The local drop in NA results in a transmission loss in the cold spot region. It is noted that the overall slope of the OTDR is 0.65 dB/m before and after the cold spot. This slope corresponds to a fiber core one way transmission loss. It is noted that the Fresnel reflection 46 from the end of the 14.5 m fiber also decreases by 2.5 dB due to the loss caused by the cold spot numerical aperture change.

Figure 7:
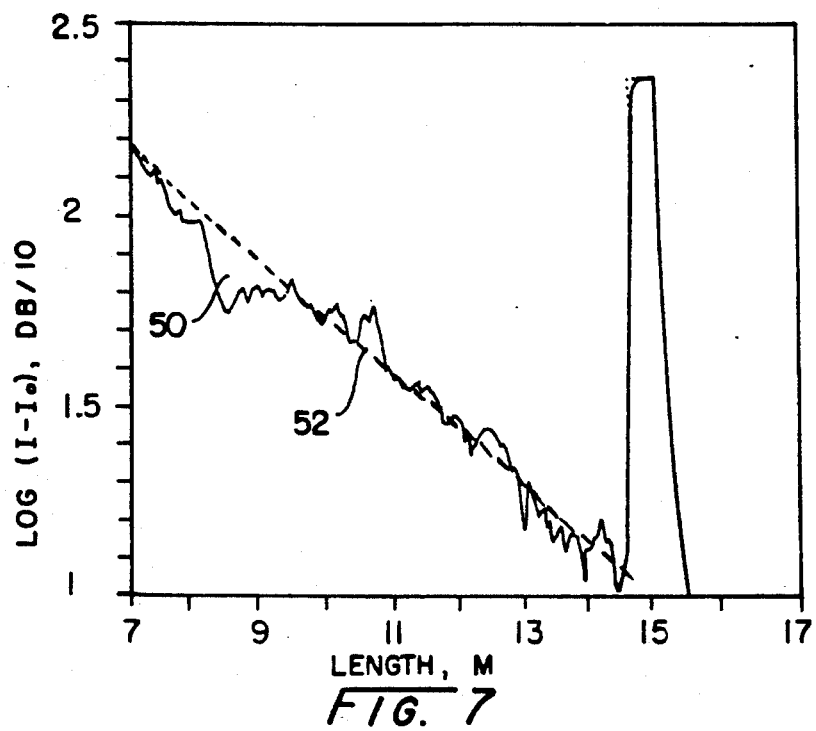
FIG. 7 shows OTDR data for a heated fiber core (50 cm of fiber heated to 150° C.) with the log $(I-I_o)$ in dB/10 (vertical axis) plotted against length in meters (horizontal axis).
Figure 8:
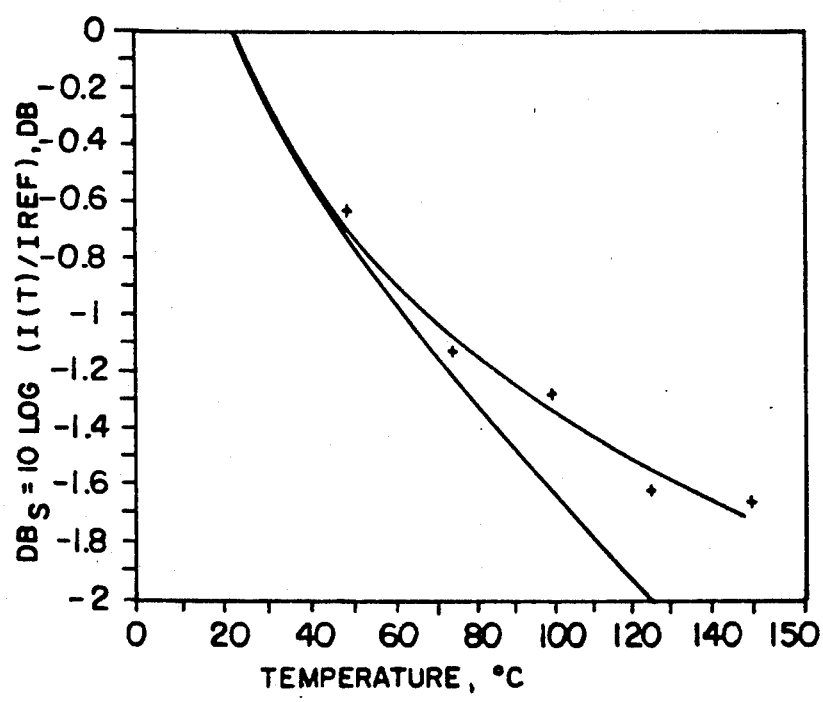
FIG. 8 is a comparison of theory and experiment for the backscattering intensity from a hot spot region. $dB_s = 10 \log (I(T)/I_{ref})$ is plotted on the vertical axis versus temperature in °C. on the horizontal axis.

In FIG. 7, an OTDR plot is shown at a reference temperature of 25° C. and a hot spot produced in 0.5 m of the fiber by heating to 150° C. It is evident from the data plot that the backscattered intensity drops in the hot spot region. The drop in light scattering intensity is equal to about −1.7 dB. After the hot spot, the scattering intensity returns to levels indicative of an unheated fiber 52. This OTDR data confirms that the hot spot sensor does not operate as a result of a loss mechanism. Rather, changes in backscattering intensity occur when the fiber is heated.

FIG. 7 shows that some noise exists in the OTDR data that could be interpreted as a temperature change. However, this noise exists on both the reference (20° C.) and the hot spot data. This noise can be dramatically reduced by using the following ratio:

$$Ratio = dB_s = 10 \, log \, ((I-I_o)/(I_R-I_o)) \qquad (7)$$

where
I = signal data
$I_R$ = reference data (20° C.) and
$I_o$ = background intensity (electronic noise).
Using the above-referencing technique and standard data smoothing processes, the temperature can be accurately measured to within ±5° C. over a wide range of temperatures (20°-150° C.).

The coating (cladding) material for this invention was prepared from a blend of diacrylate monomers, triacrylate monomers and polymers based on 2, 3, 4 or n+1 moles of a diisocyanate (isophorone, hexamethylene or toluene) to 1, 2, 3 or n moles of a polyglycol (polypropylene, polyethylene) followed by reaction with 2 moles of hydroxyethyl acrylate. Examples of typical diacrylate monomers, triacrylate monomers and urethane polymers used in this invention are shown in Tables 2, 3 and 4.

The actual coating composition used in this invention could be varied between 5 to 88 percent by weight for any of the three components (diacrylate, triacrylate and polymer) as shown in Table 5. All of the compositions contained 2 percent by weight of a photoinitiator selected from the materials shown in Table 6.

EXAMPLE I

Figure 9:
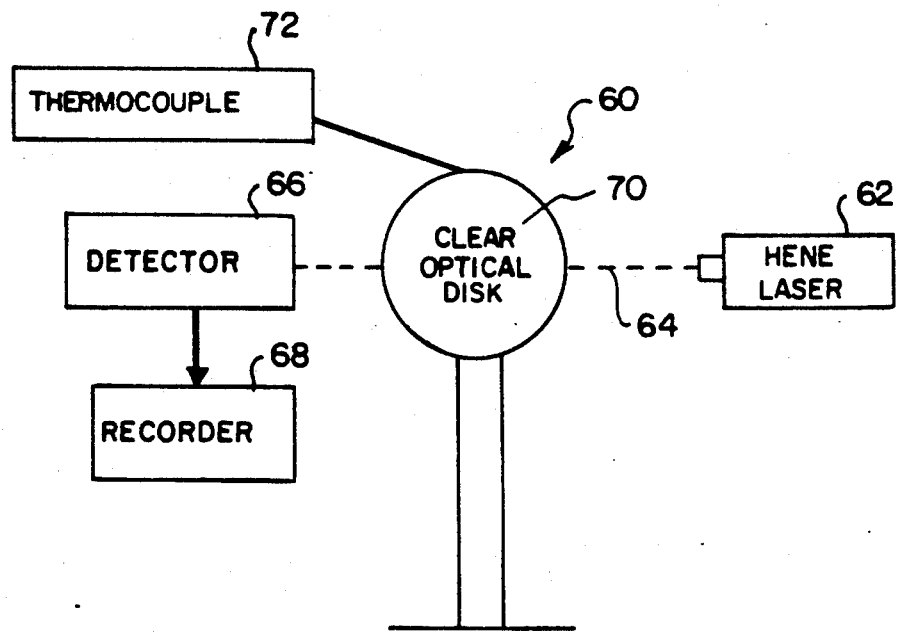
FIG. 9 is a schematic diagram of an optical disk test apparatus for testing the cladding compositions of this invention.

A coating composition consisting of 25 percent PES 186 (an acrylic functional aliphatic/aromatic urethane polymer containing polypropylene glycol units capped with toluene diisocyanate and hydroxyethel acrylate available from Polymer Systems Corporation; for other urethane acrylate polymers, see Table 4), 5 percent of trimethylolpropane triacrylate (Table 3), 60 percent of hexane dioldiacrylate (Table 2), and 2 percent Irgacure 184 (Table 6) were blended together and cured into ⅛ inch circular clear disks using two General Electric UV-sunlamps having major emission wavelengths energies at 365 nm. These clear disks 70 were placed in the apparatus 60 shown in FIG. 9 which consists of a helium-neon laser beam generator 62 producing a signal 64 that passes through the optical disk 70 to a detector 66. The detected signal is recorded with recorder 68. A thermocouple 72 is used to determine the temperature of the sample.

Figure 10:
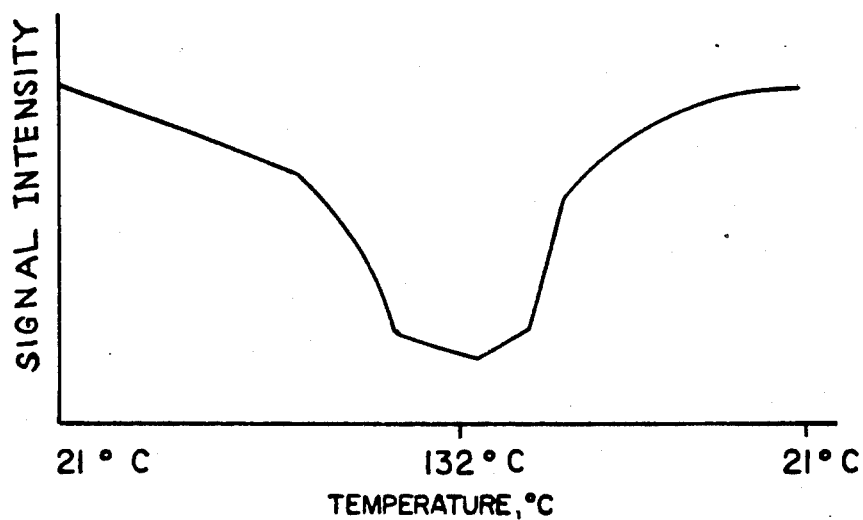
FIG. 10 shows the change in signal intensity (vertical axis) as the temperature is increased and then decreased (horizontal axis) for an optical disk formulation from Example I.

Application of heat using a heat gun or hair dryer to the optical disk caused the optical signal intensity to change as a function of temperature. Increase in the temperature caused the transmitted intensity signal to decrease while decreasing the temperature caused the signal to increase as shown in FIG. 10.

EXAMPLE II

Similar results for the Example I formulation were observed for the formulations shown in Tables 5 and 7. All of these formulations in Tables 5 and 7 exhibited the same effect, namely increase in temperature-decrease in optical signal intensity as measured in the apparatus shown in FIG. 9.

EXAMPLE III

A one-meter long borosilicate glass fiber was coated with the formulation described in Example I. This coating was cured on the glass fiber using 5 General Electric UV-sunlamps that were arranged in a somewhat circular manner over the entire length of the 1-meter long glass fiber. Thus, the Example I formulation coated fiber exhibited the same phenomena as previously described for the optical disk test arrangement described in Example I. An increase in temperature anywhere along the length of the coated optical fiber causes a change in backscattered light signal intensity. FIG. 1B shows the effect of temperature or hot spot on the specially coated (Example I formulation) borosilicate glass fiber and its light wave propagation capabilities. This effect of temperature and change in optical signal intensity was demonstrated for a 50-meter long borosilicate glass fiber core coated with the Example I formulation. The results of a hot spot or increased temperature and the change in optical signal intensity for this system are shown in FIG. 7.

EXAMPLE IV

Control Formulations

Formulations containing only one or two of the three major components listed in Table 2, 3 and 4 do not exhibit the observed change in optical signal intensity as a function of temperature. See Table 8 for additional details.

EXAMPLE V

Low Refractive Index Coatings Containing Fillers as Scattering Centers

In this example, a commercial series of silicone UV-curable polymers were obtained from Dow Corning (Number 6256-93), Desoto (Number 950-080) and Petrach Systems (PS-802). These UV-curable silicone polymers have cured film refractive index values of 1.41-1.42; 1.44 and 1.422, respectively. These materials when cured into optical disks or coated onto silica base optical fiber cores exhibited no signs or change in optical quality (scattering or opacity) as a function of increased temperature. However, when certain types of fillers, however, are added to the formulation then the desired effects are observed. Additives of anywhere from 0.005 percent to 1 percent particles (diameter 0.4 to 4 μm) quartz or polytetrafluoroethylene (refractive index of 1.46 or 1.33) to the UV curable silicone materials resulted in an optical system that changed its capability to scatter light with increased temperature in a manner similar to that shown in FIGS. 1B, 6 and 7.

TABLE 2

| DIACRYLATE MONOMERS |
|---|
| Hexane Dioldiacrylate |
| Bis Phenol-A-Ethoxylate Diacrylate |
| Polyethylene Glycol 200 Diacrylate |
| Tripropylene Glycol Diacrylate |
| 1,4-Butanediol Diacrylate |
| Bis Phenol-A-Epoxide Diacrylate |
| Neopentylglycol Diacrylate |

TABLE 3

TRIACRYLATE MONOMERS

Trimethylolpropane Triacrylate
Glyceryl Propoxylate Triacrylate
Trimethylolpropane Ethoxylate Triacrylate

TABLE 4

POLYMERS (URETHANE ACRYLATES)[1]

| | | | |
|---|---|---|---|
| Photomer 6008 | Aliphatic | Urethane | Acrylate |
| Photomer 6019 | Aliphatic | Urethane | Acrylate |
| Photomer 6890 | Aromatic | Urethane | Acrylate |
| Photomer 6022 | Aromatic | Urethane | Acrylate |
| Photomer 6783 | Aromatic | Urethane | Acrylate |
| Photomer 6184 | Aliphatic | Urethane | Acrylate |
| Photomer 6230 | Aliphatic | Urethane | Acrylate |
| Photomer 6264 | Aliphatic | Urethane | Acrylate |
| Photomer 6788 | Aliphatic | Urethane | Acrylate |
| Photomer 6827 | Aliphatic | Urethane | Acrylate |
| Photomer 6893 | Aliphatic | Urethane | Acrylate |

[1] All the above materials are commercially available from Diamond Shamrock, now part of Henkel Corporation.

TABLE 5

COATING COMPOSITIONS[1]

| Photoinitiator wt. % | Diacrylate wt. % | Triacrylate wt. % | Polymer wt. % |
|---|---|---|---|
| 2 | 5 | 5 | 88 |
| 2 | 5 | 88 | 5 |
| 2 | 88 | 5 | 5 |
| 2 | 68 | 5 | 25 |
| 2 | 25 | 5 | 68 |
| 2 | 25 | 68 | 5 |
| 2 | 30 | 30 | 38 |

[1] These coating compositions ranged in refractive index values between 1.4 and 1.5 and had solution viscosity ranges between 10 and 3,000 cps or greater.

TABLE 6

PHOTOINITIATORS

| Formulation | Tradename | Manufacturer |
|---|---|---|
| Benzil Ketals | Irgacure 651 | Ciba-Geigy |
| Hydroxyl Cyclohexyl Phenyl Ketone | Irgacure 184 | Ciba-Geigy |
| Acetophenone Derivatives | DEAP | UpJohn |
| Acetophenone Derivatives | Daracure 1173 | EM Chemical |

TABLE 7

EXAMPLE II FORMULATIONS

| Sample | PES 186 wt. % | Trimethyol propane Triacrylate wt. % | Hexanediol Diacrylate wt. % | Irgacure 184 wt. % |
|---|---|---|---|---|
| 1 | 40 | 5 | 53 | 2 |
| 2 | 40 | 20 | 38 | 2 |
| 3 | 40 | 25 | 53 | 2 |

TABLE 8

CONTROL FORMULATIONS

| PES 186 wt. % | Hexanediol Diacrylate wt. % | Trimethylol propane Triacrylate wt. % | Results |
|---|---|---|---|
| 100 | — | — | No signal change |
| — | 100 | — | No signal change |
| 50 | 50 | — | No signal change |
| 50 | — | 50 | No signal change |

It is to be understood that although the present invention has been specifically disclosed with the preferred embodiment and examples, modifications to the experimental design may be apparent to those skilled in the art and such modifications and variations are considered to be within the scope of the invention and the appended claims. It is also intended that all matter contained in the above description shall be interpreted as illustrative and not in a limiting sense, the scope of the invention being indicated by the appended claims rather than by the foregoing description: thus all changes that come within the meaning and range of equivalency of the claims are therefore intended to be embraced therein. That is, the following claims are intended to cover all of the generic and specific features of the invention herein described, and all statements of the scope of the invention which, as a matter of language, fall therebetween. Furthermore, it is to be understood that in the following claims, ingredients or compounds recited in the singular are intended to include compatible mixtures of such ingredients wherever the sense permits.

We claim:

1. A distributed fiber-optic sensor comprising:
   a. an optical fiber core having a cladding that produces a change in light scattering in said cladding in response to a change in the environment of said cladding wherein said change in light scattering in said cladding is coupled into said optical fiber core to produce a change in intensity of backscattered light in said optical fiber core and
   b. a means for sensing said change in intensity of said backscattered light.

2. The distributed fiber-optic sensor according to claim 1 wherein said change in intensity of said backscattered light in said optical fiber core is caused by refractive index inhomogeneities in said cladding.

3. The distributed fiber-optic sensor according to claim 1 wherein said change in intensity of said backscattered light in said optical fiber core is due to a change in Rayleigh scattering in said cladding.

4. The distributed fiber-optic sensor according to claim 1 wherein said sensing means is capable of determining the position of said change in said intensity of said backscattered light along the length of said optical fiber.

5. The distributed fiber-optic sensor according to claim 4 wherein said sensing means is an optical time domain reflectometer.

6. The distributed fiber-optic sensor according to claim 1 wherein the refractive index of said cladding material is less than the refractive index of said optical fiber core.

7. The distributed fiber-optic sensor according to claim 6 wherein the difference between said refractive index of said cladding material and said refractive index of said optical fiber core under initial environmental conditions is about 0.005 to about 0.05.

8. The distributed fiber-optic sensor according to claim 7 wherein the difference between said refractive index of said cladding material and said refractive index of said optical fiber core under initial environmental conditions is about 0.01 to about 0.03.

9. The distributed fiber-optic sensor according to claim 6 wherein said refractive index of said optical fiber core remains essentially constant with respect to said change in said environment of said cladding.

10. The distributed fiber-optic sensor according to claim 9 wherein said refractive index of said cladding changes by more than 0.01 with respect to a predetermined change in said environment.

11. The distributed fiber-optic sensor according to claim 10 wherein said refractive index of said cladding changes by more than 0.02 with respect to a predetermined change in said environment.

12. The distributed fiber-optic sensor according to claim 11 wherein said refractive index of said cladding changes by more than 0.05 with respect to a predetermined change in said environment.

13. The distributed fiber-optic sensor according to claim 10 wherein said change in said refractive index of said cladding with respect to said change in said environment is more than about 100 times greater than the change in said refractive index of said core.

14. The distributed fiber-optic sensor according to claim 13 wherein said change in said refractive index of said cladding with respect to said change in said environment is more than about 700 times greater than the change in said refractive index of said core.

15. The distributed fiber-optic sensor according to claim 1 wherein said change in said environment is a change in temperature.

16. The distributed fiber-optic sensor according to claim 15 wherein said refractive index of said cladding changes with respect to said temperature of said cladding at a rate of more than about $1.0 \times 10^{-4}/°$ C.

17. The distributed fiber-optic sensor according to claim 16 wherein said refractive index of said cladding changes with respect to said temperature of said cladding at a rate of more than about $3.0 \times 10^{-4}/°$ C.

18. The distributed fiber-optic sensor according to claim 17 wherein said refractive index of said cladding changes with respect to said temperature of said cladding at a rate of more than about $7.0 \times 10^{-4}/°$ C.

19. The distributed fiber-optic sensor according to claim 1 wherein said cladding material is less than about $5.0 \times 10^{-3}$ inches thick.

20. The distributed fiber-optic sensor according to claim 19 wherein said cladding material is about $1.5 \times 10^{-3}$ to about $3.0 \times 10^{-3}$ inches thick.

21. The distributed fiber-optic sensor according to claim 1 wherein said cladding material is formed from a liquid that is subsequently polymerized.

22. The distributed fiber-optic sensor according to claim 21 wherein said liquid is subsequently polymerized using ultraviolet light.

23. The distributed fiber-optic sensor according to claim 1 wherein said cladding material is a thermoplastic polymer formulation having light scattering centers responsive to said change in said environment.

24. The distributed fiber-optic sensor according to claim 23 wherein said change in said environment is a change in temperature.

25. The distributed fiber-optic sensor according to claim 23 with said thermoplastic polymer formulation comprising a diacrylate monomer, a triacrylate monomer and a urethane acrylate polymer based on a diisocyanate, polyglycol and an acrylate.

26. The distributed fiber-optic sensor according to claim 25 with said urethane acrylate polymer comprising polypropylene glycol units capped with toluene diisocyanate and hydroxyethyl acrylate.

27. The distributed fiber-optic sensor according to claim 25 with said diacrylate monomer being hexanediol diacrylate.

28. The distributed fiber-optic sensor according to claim 25 with said triacrylate monomer being trimethylolpropane triacrylate.

29. The distributed fiber-optic sensor according to claim 25 with said thermoplastic polymer formulation further comprising a photoinitiator.

30. The distributed fiber-optic sensor according to claim 1 with said cladding material comprising a light-scattering filler.

31. The distributed fiber-optic sensor according to claim 30 with said light-scattering filler selected from the group of fillers consisting of quartz and polytetrafluoroethylene.

32. The distributed fiber-optic sensor according to claim 30 further comprising a UV-curable silicone polymer.

* * * * *